United States Patent
Niu et al.

(10) Patent No.: US 10,628,011 B2
(45) Date of Patent: Apr. 21, 2020

(54) MEDICAL DEVICES, METHOD AND APPARATUS FOR ADJUSTING A TIME RANGE OF A TREND CHART

(71) Applicant: SHENZHEN MINDRAY BIO-MEDICAL ELECTRONICS CO., LTD., Shenzhen (CN)

(72) Inventors: Wenke Niu, Shenzhen (CN); Ying Yin, Shenzhen (CN); Hao Hu, Shenzhen (CN)

(73) Assignees: SHENZHEN MINDRAY BIO-MEDICAL ELECTRONICS CO., LTD., Shenzhen (CN); SHENZHEN MINDRAY SCIENTIFIC CO., LTD., Shenzhen (CN)

( * ) Notice: Subject to any disclaimer, the term of this patent is extended or adjusted under 35 U.S.C. 154(b) by 332 days.

(21) Appl. No.: 15/196,491

(22) Filed: Jun. 29, 2016

(65) Prior Publication Data

US 2017/0177199 A1    Jun. 22, 2017

Related U.S. Application Data

(63) Continuation of application No. PCT/CN2014/077335, filed on May 13, 2014.

(30) Foreign Application Priority Data

Dec. 31, 2013    (CN) .......................... 2013 1 0754672

(51) Int. Cl.
*G06F 3/048*     (2013.01)
*G06F 3/0484*    (2013.01)
(Continued)

(52) U.S. Cl.
CPC ...... *G06F 3/04845* (2013.01); *G06F 3/04847* (2013.01); *G06F 3/04883* (2013.01);
(Continued)

(58) Field of Classification Search
CPC .............................. G06F 3/048; G06T 11/206
See application file for complete search history.

(56) References Cited

U.S. PATENT DOCUMENTS

| | | | | |
|---|---|---|---|---|
| 2012/0044281 A1* | 2/2012 | Kang | ................... | G09G 3/3413 345/690 |
| 2012/0143020 A1* | 6/2012 | Bordoley | .............. | A61B 5/1114 600/301 |

(Continued)

FOREIGN PATENT DOCUMENTS

| | | |
|---|---|---|
| CN | 101876877 A | 11/2010 |
| CN | 102841749 A | 12/2012 |

(Continued)

*Primary Examiner* — Xuyang Xia
(74) *Attorney, Agent, or Firm* — Kory D. Christensen (57) ABSTRACT

Disclosed are a method and apparatus for adjusting resolution of medical image. When adjusting resolution, a touch screen is used for display and input. A the method may include: detecting a touch operation inputted by a user through the touch screen under an interface state for displaying a digital image and generating touch information; identifying motion of the user's touch operation in accordance with the touch information and generating motion information; judging whether the detected touch motion meets a predetermined condition for adjusting resolution; if yes, computing an adjusted resolution based on the motion information and a predetermined computing method and displaying data with the adjusted resolution on a region desired to be adjusted on the interface; and when the detected touch motion fails to meet the predetermined (Continued)

condition for adjusting resolution, maintaining the display on the interface with an original resolution on the interface.

17 Claims, 8 Drawing Sheets

(51) Int. Cl.
*G06T 3/00* (2006.01)
*G06F 3/0488* (2013.01)
*G06F 19/00* (2018.01)
*G06T 3/40* (2006.01)
*G06T 11/20* (2006.01)

(52) U.S. Cl.
CPC .......... *G06F 19/321* (2013.01); *G06T 3/0012* (2013.01); *G06T 3/40* (2013.01); *G06F 2203/04808* (2013.01); *G06T 11/206* (2013.01); *G06T 2200/24* (2013.01); *G06T 2210/41* (2013.01)

(56) References Cited

U.S. PATENT DOCUMENTS

| | | | | |
|---|---|---|---|---|
| 2014/0215382 A1* | 7/2014 | Engel | ................... | G06F 3/04883 715/784 |
| 2014/0282171 A1* | 9/2014 | Glueck | ............... | G06F 3/04847 715/771 |
| 2014/0359435 A1* | 12/2014 | Zheng | ................... | G06F 3/0488 715/702 |
| 2015/0133743 A1* | 5/2015 | Baron | ................... | G16H 40/40 600/301 |
| 2015/0248534 A1* | 9/2015 | Krzywicki | .......... | G06F 3/04847 715/771 |

FOREIGN PATENT DOCUMENTS

| | | |
|---|---|---|
| CN | 202821639 U | 3/2013 |
| CN | 103006201 A | 4/2013 |
| CN | 103181752 A | 7/2013 |

\* cited by examiner

MEDICAL DEVICES, METHOD AND APPARATUS FOR ADJUSTING A TIME RANGE OF A TREND CHART

TECHNICAL FIELD

The present application relates to adjustment for resolution of a digital image.

BACKGROUND

Figure 1:
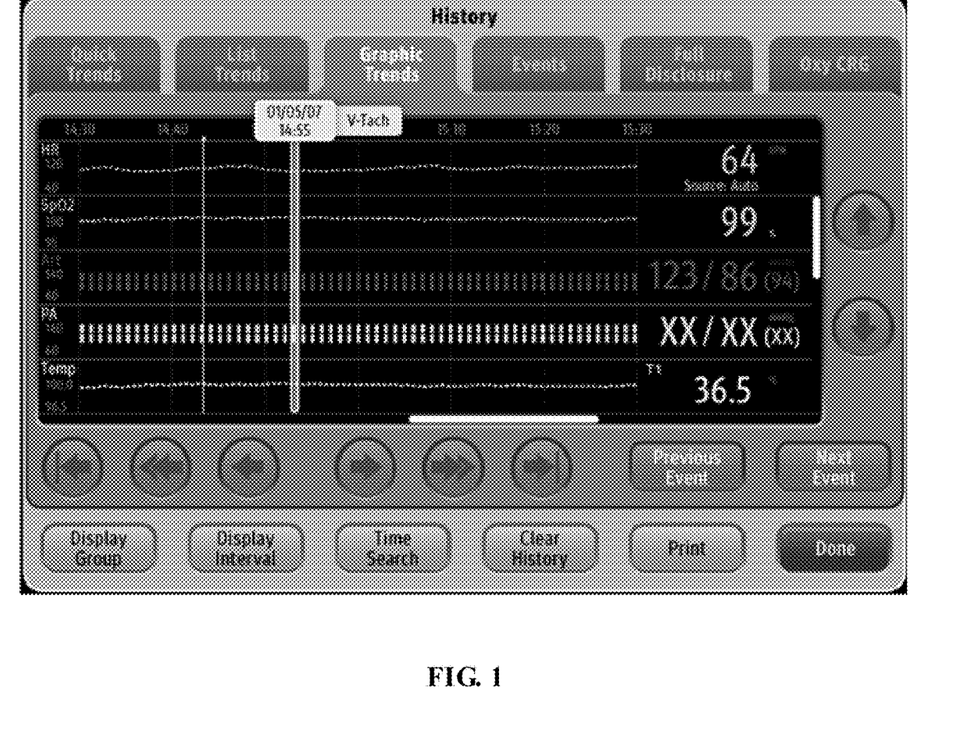
FIG. 1 schematically illustrates displaying a trend chart on a monitor.

Monitors are used to detect and show one or more parameters of a patient's life signs in a clinical context; For example, the patient's blood pressure, blood oxygen, pulse, heart rate, electrocardiogram (ECG) and electroencephalogram (EEG) are monitored and displayed by a monitor. A trend chart, displayed on the monitor's interface, is used to illustrate a trend toward the patient's life signs to express time-varying status of the patient's life sign parameters. FIG. 1 shows an example of the trend chart displaying the patient's physiological parameter monitored within a time period, in which different rows show different parameters. Left side of each row displays information about parameter name; while in the middle, trend data during current period are represented graphically on different time points in horizontal direction, and the cursor is used for displaying specific data of current time at right side of the interface when a user browses data. The lines not appeared on the interface can be displayed by scrolling manipulation. Users often browse with different resolutions frequently. To help a doctor to carry out an all-round analysis on patient's life sign parameters from macro and micro point of view for clinical diagnosis, the trend chart is designed to be adjustable in resolution. The resolution shows a metric of time range under current display width. The higher the resolution, the smaller the time period shown under a same display width.

Figure 2:
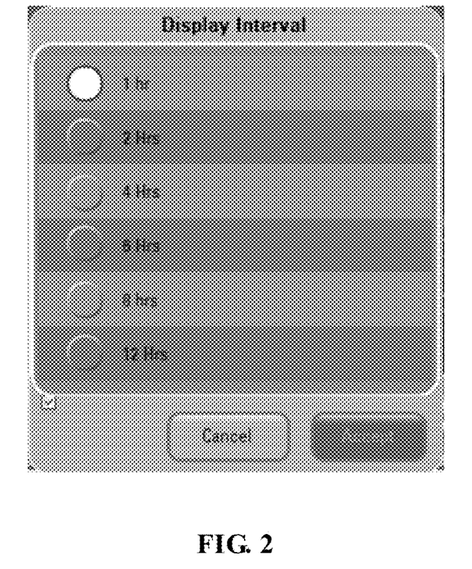
FIG. 2 schematically illustrates a resolution setting interface.

It is usually necessary to open a special interface to adjust resolutions of the trend chart on patient monitors nowadays. For example, in FIG. 2, a dialog box is opened to set resolutions by choosing Display Interval button shown in FIG. 1. The data would be shown on the interface with the desired resolution after being set effectively by the user. Operations of setting resolutions at the interface are usually performed by a knob or a mouse during adjusting the resolution. Due to so many operating steps, the operation is inconvenient and not intuitive, reducing usability of browsing trend charts and operating devices. Function of adjusting resolutions helps doctors better analyze patients' data.

SUMMARY

The present application provides an adjusting method and an apparatus for directly adjusting image resolution on an image display interface, as well as a medical device using the method and the apparatus, which may reduce operating steps of adjusting resolution for a user.

According to a first aspect of the present application, a method for adjusting resolution of a digital image, which is based on using a touch screen as a display and input device, is provided in the present application. The method may include:

detecting touch operation inputted by a user through the touch screen under a state of displaying the digital image on an interface, and generating touch information;

identifying user's motion for the touch operation in accordance with the touch information and generating motion information;

judging whether the touch motion meets a predetermined condition for adjusting resolution;

if yes, computing adjusted resolution based on the motion information and a predetermined computing method, and displaying the digital image with the adjusted resolution on a region desired to be adjusted on the interface; and if no, maintaining the digital image displayed on the interface with original resolution.

The present application may also provide another method for adjusting resolution of a digital image, which is based on using a touch screen as a display and input device. The method may include:

detecting touch operation inputted by a user through the touch screen under a state of displaying the digital image on an interface, and generating touch information;

identifying user's motion for the touch operation in accordance with the touch information and generating motion information; and judging whether the touch motion corresponds to a predetermined activation for adjusting resolution: if no, maintaining original resolution on the interface; if yes, adjusting resolution on the interface, which may includes the following steps:

detecting touch operation inputted by the user through the touch screen, and generating the touch information;

identifying the user's motion for the touch operation in accordance with the touch information and generating motion information;

judging whether the touch motion meets a predetermined condition for adjusting resolution;

if yes, computing adjusted resolution based on the motion information and a predetermined computing method, and displaying the digital image with the adjusted resolution on a region desired to be adjusted on the interface; and if no, maintaining the digital image displayed on the interface with original resolution.

According to a second aspect of the present application, an apparatus for adjusting resolution of a digital image, which is based on using a touch screen as a display and input device, is provided in the present application. The apparatus may include:

a motion identifying unit for receiving touch information outputted by the touch screen, identifying motion of user's touch operation in accordance with the touch information and generating motion information;

an adjustment judging unit for judging whether the touch motion detected by the motion identifying unit meets a predetermined condition for adjusting resolution;

a resolution computing unit for if the adjustment judging unit determines that the touch motion meets the predetermined condition for adjusting resolution, computing an adjusted resolution based on the motion information and a predetermined computing method; and a displaying unit for displaying the digital image with the adjusted resolution outputted by the resolution computing unit on a region desired to be adjusted on the interface, and maintaining the digital image displayed on the interface with original resolution if the detected touch motion fails to meet the predetermined condition for adjusting resolution.

The present application may also provide another apparatus for adjusting resolution of a digital image. The apparatus may include:

a motion identifying unit for receiving touch information outputted by the touch screen, identifying motion of user's touch operation in accordance with the touch information and generating motion information;

an adjustment activation judging unit for judging whether the detected touch motion corresponds to a predetermined activation for the adjusting resolution, if no, maintaining the digital image displayed on the interface with original resolution; if the detected touch motion corresponds to the predetermined activation for the adjusting resolution, starting a process of adjusting resolution on the interface;

an adjustment judging unit for, after starting the process of adjusting resolution by the adjustment activation judging unit, judging whether the touch motion detected by the motion identifying unit meets a predetermined condition for adjusting resolution;

a resolution computing unit for, if the adjustment judging unit determines that the touch motion meets the predetermined condition for adjusting resolution, computing adjusted resolution based on the motion information and a predetermined computing method; and a displaying unit for displaying the digital image with the adjusted resolution outputted by the resolution computing unit on a region desired to be adjusted on the interface, and maintaining the digital image displayed on the interface with original resolution if the detected touch motion fails to meet the predetermined condition for adjusting resolution.

According to a third aspect of the present application, a medical equipment is provided in the present application. The medical equipment may include:

a data detecting device for detecting a patient's life sign parameters;

a data processing module with an input terminal coupled to an output terminal of the data detecting device for analyzing and processing the life sign parameters to generate visual display data;

a touch screen, which is a multitouch screen connected to the data processing module by signals, is configured for providing a visual trend chart of the life sign parameters and a user input interface for a monitor and outputting touch information when sensing a user's operation; and the above-mentioned apparatus for adjusting resolution of a digital image, wherein the apparatus for adjusting the resolution is connected to the touch screen and the data processing module by signals respectively, and receives touch information outputted by the touch screen, and outputs a displaying result with adjusted resolution to the data processing module.

By means of detecting a user's touch operation on the touch screen and calculating the user's desired resolution based on the user's touch motion, the present application may accomplish the goal of directly adjusting image resolution on an image display interface and reducing the user's operating steps. Since the operation may largely rely on the user's touch operation, it is more in line with people's operating habit, more intuitive, simple and convenient, which may improve efficiency and usability of browsing data.

DETAILED DESCRIPTIONS

The disclosure will be further described by the following detailed description of embodiments with the accompanying drawings.

Many devices can be used to display gathered image data. In an embodiment of the present application, images may include diagrams, graphs and waveform; and waveform may include trend charts of time-varying data. When adjusting resolution of an image, an instruction of resolution adjustment may be inputted by a user through a touch screen, the resolution of the image desired by the user may be adjusted based on the user's touch motion, and data may be displayed with the adjusted resolution. A trend chart shown on a clinical monitoring device is taken as an example in the followings; however, those skilled in the art will appreciate that, the solution of the resolution adjustment in the present application may also be applicable to other medical equipment or image display devices, for example, adjusting different resolution for parameters, waveform, compression waveform and image data applied in a central station, a defibrillator, or an anesthesia machine.

First Embodiment

Figure 3:
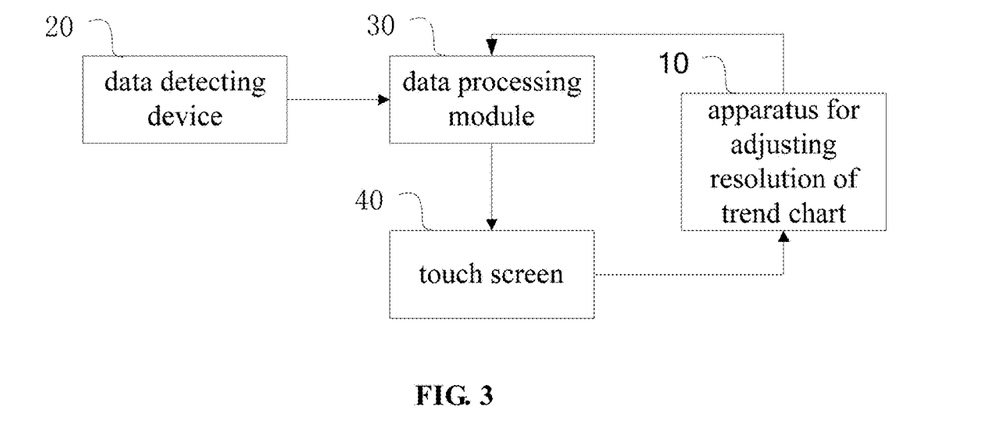
FIG. 3 schematically illustrates a structure of a monitoring device in an embodiment of the present application.

In a specific example, a structure of the monitoring device shown in FIG. 3 may include an apparatus 10 for adjusting resolution of a trend chart, a data detecting device 20, a data processing module 30 and a touch screen 40. The data detecting device 20 may be used for detecting a patient's life sign parameters such as blood pressure, heart rate, blood oxygen, etc. The data processing module 30 with an input terminal coupled to an output terminal of the data detecting device 20 may be used for receiving the life sign parameters detected by the data detecting device 20, analyzing and processing the life sign parameters to generate visual display data. The touch screen 40, which may be a multitouch screen, may be connected to the data processing module 30 by signals and used for providing a visual trend chart of the life sign parameters and a user input interface for the monitoring device and outputting touch information when sensing a user's operation. The apparatus 10 for adjusting resolution of a trend chart may connect to the touch screen 40 and the data processing module 30 by signals respectively, and receive touch information outputted by the touch screen 40, and output a displaying result with adjusted resolution to the data processing module 30.

Figure 4:
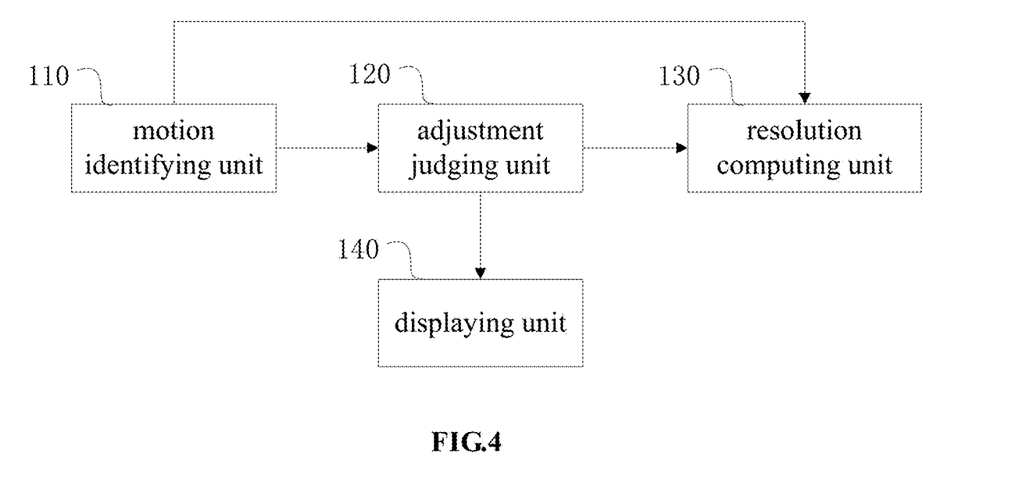
FIG. 4 schematically illustrates a structure of an apparatus for adjusting resolution of a trend chart in an embodiment of the present application.

In a specific example, the structure of the apparatus 10 for adjusting resolution of a trend chart schematically shown in FIG. 4 may include a motion identifying unit 110, an adjustment judging unit 120, a resolution computing unit 130 and a displaying unit 140.

The motion identifying unit 110 may be used for receiving touch information outputted by the touch screen, identifying motion of a user's touch operation in accordance with the touch information, and generating motion information.

The adjustment judging unit 120 may be used for judging whether the touch motion detected by the motion identifying unit 110 meets a predetermined condition for adjusting resolution. A specific way to judge by the adjustment judging unit 120 is to determine whether the touch motion meets the predetermined condition for adjusting resolution based on a result of judging whether the touch motion corresponds to a predetermined motion for adjusting resolution. The adjustment judging unit 120 may also perform a judgment with help of location information of the touch operation in the motion information; that is, judging whether the touch motion is located at a display region of the trend chart; if no, the touch motion may be regarded as failing to meet the predetermined condition for adjusting resolution; and if yes, the trend chart corresponding to the touch operation may be regarded as a trend chart desired to be adjusted.

Figure 5:
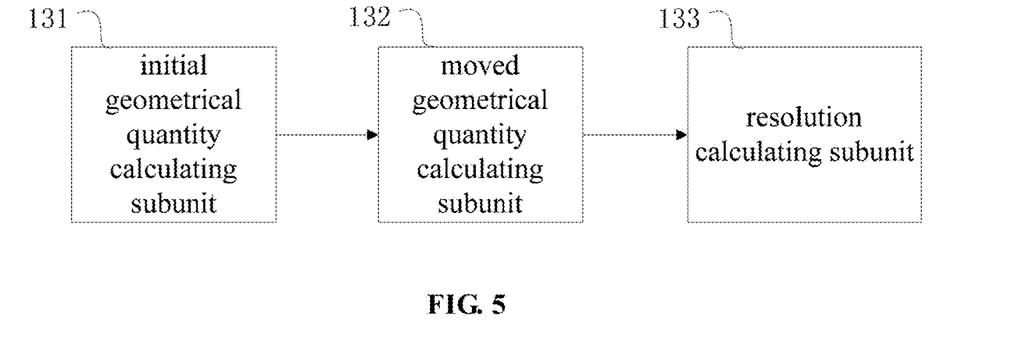
FIG. 5 schematically illustrates a structure of a resolution computing unit in an embodiment of the present application.

The resolution computing unit 130 may be used for computing adjusted resolution of the trend chart based on the motion information generated by the motion identifying unit 110 and a predetermined computing method if the adjustment judging unit 120 determines that the touch motion meets the predetermined condition for adjusting resolution. When the predetermined motion for adjusting resolution includes sliding touch points, a structure of the resolution computing unit which may include an initial geometrical quantity calculating subunit 131, a moved geometrical quantity calculating subunit 132 and a resolution calculating subunit 133 may be shown in FIG. 5. The initial geometrical quantity calculating subunit 131 may be used for calculating initial geometrical quantity of the plurality of touch points based on the location information of the plurality of touch points in the motion information when they initially contact the touch screen. The moved geometrical quantity calculating subunit 132 may be used for calculating after-sliding geometrical quantity for the plurality of touch points based on final location information of the plurality of touch points in the motion information. The final location information of the plurality of touch points may be referred to a current location information obtained after the location information of the plurality of touch points remains unchanged for a preset time period; or after detecting that the plurality of touch points departs from the touch screen, location information of the plurality of touch points obtained at the last time of detection may be referred to the final location information. The resolution calculating subunit 133 may be used for calculating the adjusted resolution based on a computational formula, for example, the adjusted resolution may be calculated by using a relationship that a ratio of the initial geometrical quantity to the moved geometrical quantity equals to a ratio of unadjusted resolution to adjusted resolution.

The displaying unit 140 may be used for displaying the digital image with the adjusted resolution outputted by the resolution computing unit 130 on a region desired to be adjusted on the interface, and maintaining the digital image displayed on the interface with original resolution if the touch motion detected by the adjustment judging unit 120 fails to meet the predetermined condition for adjusting resolution.

Figure 6:
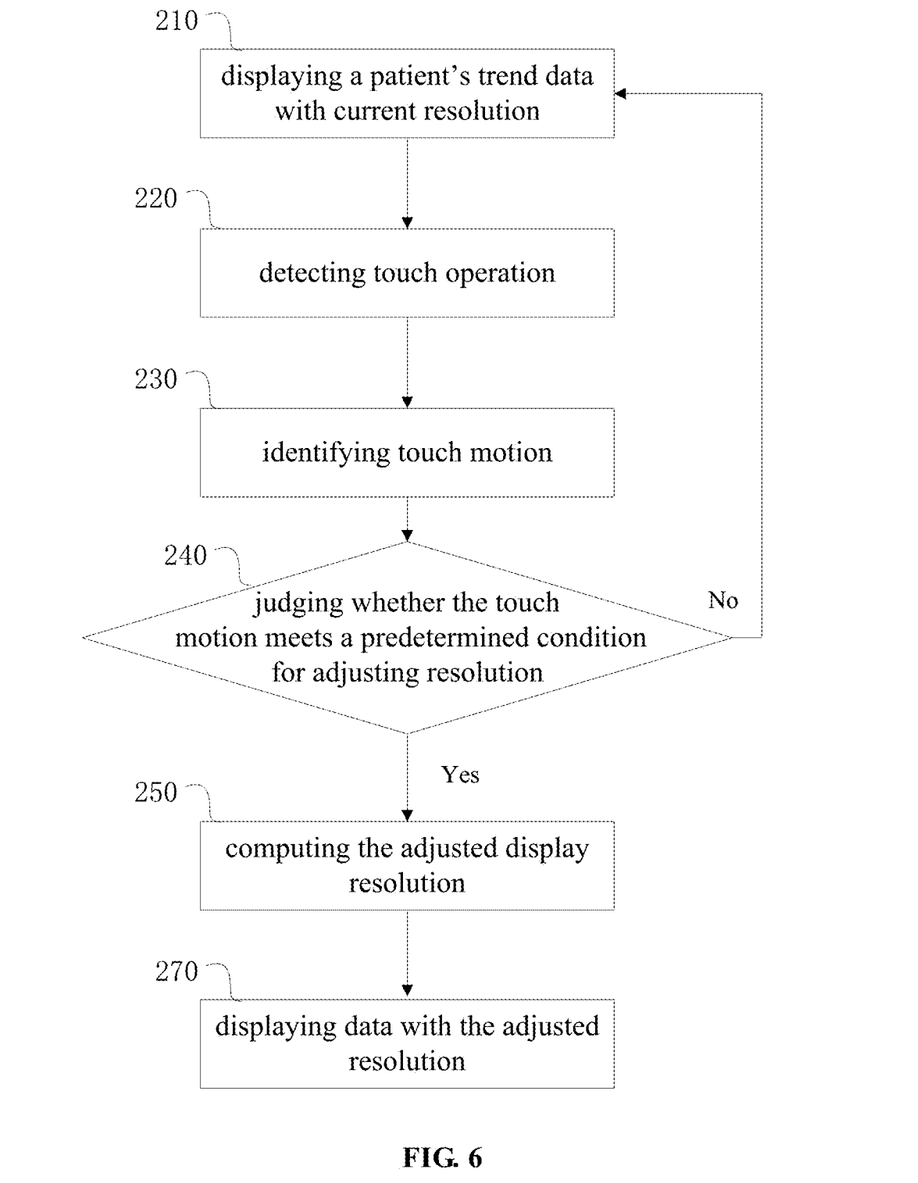
FIG. 6 schematically illustrates a flowchart of adjusting resolution in a trend chart in an embodiment of the present application.

Based on the aforesaid monitoring device, a procedure of adjusting resolution of a trend chart is schematically shown in FIG. 6, which may include the following steps.

Step 210, keeping an interface of the trend chart open on the monitor and displaying a patient's trend data with a current resolution.

Step 220, detecting touch operation. When a user desires to adjust the resolution on the interface, the user may contact with the touch screen and perform touch operation to change the display resolution to be that desired by the user. The step is an interaction between the user and the monitor. When the user contacts the touch screen, the system may start to response the user's touch operation, during which various touch-related information based on the contact between the user and the touch screen. The touch information may largely be information involved in a touch point, which may include but not limit to touch point coordinate, touch time and/or pressure at a touch point. The motion identifying unit may detect touch operation inputted by the user through the touch screen under interface state for displaying the trend chart, and generate touch information.

Step 230, identifying touch motion. The touch information of the touch point may refer to information of a single touch point, not motion information. It is need to identify the user's motion on the basis of information about touch point and generate user's motion information. The motion information may include but not limit to movement, direction of the movement, movement speed (value and direction) and/or acceleration of movement (value and direction).

Step 240, judging whether the touch motion meets a predetermined condition for adjusting resolution, if yes, performing step 250, otherwise performing the step 210 where the trend chart on the interface may be maintained with original resolution. There are two conditions needed to be fulfilled when adjusting the resolution of the trend chart. One is to know which trend chart needed to be adjusted, which can be determined by default settings or user's choices. Another is to judge whether the touch motion corresponds to a predetermined motion for adjusting resolution. When the trend chart needed to be adjusted can be determined by default settings, it is only need to determine whether the touch motion meets the predetermined condition for adjusting resolution based on a result of judging whether the touch motion corresponds to a predetermined motion for adjusting resolution. If the touch motion corresponds to the predetermined motion for adjusting resolution, it means that the touch motion may meet the predetermined condition for adjusting resolution, and it is allowed to adjust the default resolution of the trend chart. If the touch motion fails to correspond to the predetermined motion for adjusting resolution, it means that the touch motion may fail to meet the predetermined condition for adjusting resolution, and it is forbidden to adjust the default resolution of the trend chart. When the trend chart needed to be adjusted can be determined by user's choices, judging whether the touch motion meets the predetermined condition for adjusting resolution may include:

a determining trend chart desired to be adjusted step for judging whether the touch motion is located at a display region of the trend chart based on the location information of the touch operation, If no, regarding the touch motion as failing to meet the predetermined condition for adjusting resolution, and performing next step for judging touch motion; and a judging touch motion step for determining whether the touch motion meets the predetermined condition for adjusting resolution based on a result of judging whether the touch motion corresponds to a predetermined motion for adjusting resolution. If the touch motion fails to correspond to the predetermined motion for adjusting resolution, the touch motion may be regarded as failing to meet the predetermined condition for adjusting resolution, and it is forbidden to adjust the default resolution of the trend chart.

If the position coordinates of the touch motion is located at the display region of the trend chart and the touch motion corresponds to the predetermined motion for adjusting resolution, that is, both of the above-mentioned conditions are met, the touch motion is regarded as meeting the predetermined condition for adjusting resolution, and it is allowed to adjust the resolution of the trend chart desired to be adjusted. If any one of the conditions fails to meet, it is regarded as failing to meet the predetermined condition for adjusting resolution, and it is forbidden to adjust the resolution of the trend chart.

Step 250, computing the adjusted display resolution of the trend chart on the basis of the motion information and a predetermined computing method.

In this step, the computing method of resolution may be determined in accordance with mode for adjusting resolution and a predetermined motion for adjusting resolution.

There can be two kinds of modes for adjusting resolution as follows:

1. identified classification resolution: which may support several types of identified resolution arranged in ascending order. For example, there may provide resolution of (1, 2, 3, 4, 5, 6, 7, 8, 9, 10). The resolution may be adjusted to a corresponding level on the basis of the touch motion. Such mode may be a main way to set resolution through dialogs.

2. dynamic range resolution: which may support adjustment within a certain dynamic. For example, if screen resolution is ranged among (Range1, Range2), the resolution can be any one value within the range, and the specific value thereof can be obtained by calculation.

There can be several kinds of the predetermined motion for adjusting resolution as follows:

1. Touch operation with a single finger; the judged touch information may be changes of touching position of the single finger. For example, when a single finger is moving along a direction, the adjustment of resolution can be calculate based on the sliding distance. In such case, the adjusting motion of resolution is a motion of a single touch point. For example, when the adjusting mode is the identified classification resolution, the resolution is arranged in ascending order, the adjusting motion of resolution can be set to be a click of a single touch point, then the resolution can be adjusted to be increased or decreased among the resolution group based on the touch motion; that is, when providing a resolution group of (1, 2, 3, 4, 5, 6, 7, 8, 9, 10), if the current resolution is 5, a new resolution may be 6 under a motion representing increasing resolution, and a new resolution may be 4 under a motion representing decreasing resolution. When the adjusting mode is the dynamic range resolution, the adjusting motion of resolution can be set by sliding a single touch point, and the resolution calculating unit can calculate the adjusted resolution based on the sliding direction and distance of the single touch point. For example, sliding left may represent decreasing resolution, sliding right may represent increasing resolution, and sliding a preset distance every time may represent increasing or decreasing one level or a preset value.

2. Touch operation with multi fingers; the judged touch information may include information of touch points, and distance information of the touch points. The predetermined motion for adjusting resolution may be sliding multiple touch points, then a predetermined calculation method may include as follows:

calculating initial geometrical quantity for the plurality of touch points based on location information of the plurality of touch points in the motion information when they initially contact the touch screen;

calculating after-sliding geometrical quantity for the plurality of touch points based on final location information of the plurality of touch points in the motion information; and calculating the adjusted resolution based on the following formula:

$$G1/G2 = Precise1/Precise2$$

where G1 is the initial geometrical quantity, G2 is the after-sliding geometrical quantity, Precise1 is the original resolution and Precise2 is the adjusted resolution.

For example, when the predetermined motion for adjusting resolution is sliding two touch points, the resolution can be adjusted with a distance obtained by calculating the distance between two fingers. The motion information which may be mainly used includes information of initial and last touch points. The information of initial touch points may be generated when the user's two fingers contact the touch screen. With sliding the two fingers on the touch screen, the resolution may be decreased as the distance between the two fingers reduces, and the displaying time period on a single screen may become larger; while the resolution may be increased as the distance between the two fingers enlarges, and the displaying time period on a single screen may become smaller. The motion may be considered to be finished when the two fingers leave the touch screen. It is assumed that the two fingers are defined as Finger A and Finger B, the coordinate of a touch point for the motion at a certain moment is (Xfa,Yfa) (Xfb,Yfb), where Xfa and Xfb are coordinates of horizontal direction, Yfa and Yfb are coordinates of vertical direction, and the coordinate of the two fingers at the certain moment is defined as a quaternion (Xfa,Yfa,Xfb,Yfb).

When the position of the initial touch point is (Xfa1,Yfa1, Xfb1,Yfb1), the position of the last touch point is (Xfa2, Yfa2,Xfb2,Yfb2), where Xa1<Xa2, Xb1<Xb2, and given that the original resolution of the interface is Precise1, the adjusted resolution is Precise2; then the adjusted resolution may be required to meet the following formula:

$$(Xa1-Xb1)/(Xa2-Xb2) = Precise1/Precise2$$

The formula, having an interface effect that the time range displayed between Xa1 and Xb1 may be identical to that between Xa2 and Xb2, is a schematic formula without considering boundary conditions.

When the predetermined motion for adjusting resolution includes sliding at least three (including three) touch points, the adjusted resolution can be calculated by an area of a geometrical shape enclosed by the at least three touch points.

3. The motion to increase or decrease the resolution. A unit of resolution may be predefined by the system to be increased or decreased for every motion; for example, a shorten sliding movement in a certain direction can be sliding a single finger or multiple fingers, a motion may be regarded as an effective adjusting movement when the sliding speed is greater than a certain speed, then the resolution computing unit may progressively increase or decrease the original resolution according to the direction and the number of the slide.

Step 270, displaying the digital image with the adjusted resolution on a region desired to be adjusted on the interface.

Second Embodiment

When displaying the trend chart with the adjusted resolution on a region desired to be adjusted on the interface, the displayed points of the trend chart can be fixed data points, or data points changing with resolution.

Unlike the first embodiment, in this embodiment there may define various data points needed to be displayed for different resolution or different scope of resolution, and it is need to determined corresponding data points of the resolution determined to be adjusted. The displayable data points corresponding to different resolution may be determined by the following manners.

Defining displayable data under different resolution: in which the displayable data points corresponding to the adjusted resolution may be determined on the basis of different data sampling rate corresponding to different resolution. For example, for the identified classification resolution (1, 2, 3, 4, 5, 6, 7, 8, 9, 10), data points displayed under such ten kinds of resolution may be defined respectively, while for the dynamic range resolution (Range1, Range2), the range is needed to be divided to determine displayable points corresponding to different range.

Defining displayability of each data point under different resolution: which may define whether data can be displayed under different resolution, and may determine displayable data points corresponding to adjusted resolution on the basis of displayability of data points under different resolution. For example, for the identified classification resolution (1, 2, 3, 4, 5, 6, 7, 8, 9, 10), a data point P1 is defined to be displayable when point P1 is greater than or equal to 5 and undisplayable when P1 is smaller than 5; while for the dynamic range resolution (Range1, Range2), a certain resolution PrceiseA within the range is set to be a threshold, then the point P1 is displayable with a resolution greater than PrceiseA and undisplayable with a resolution smaller than PrceiseA.

Figure 7:
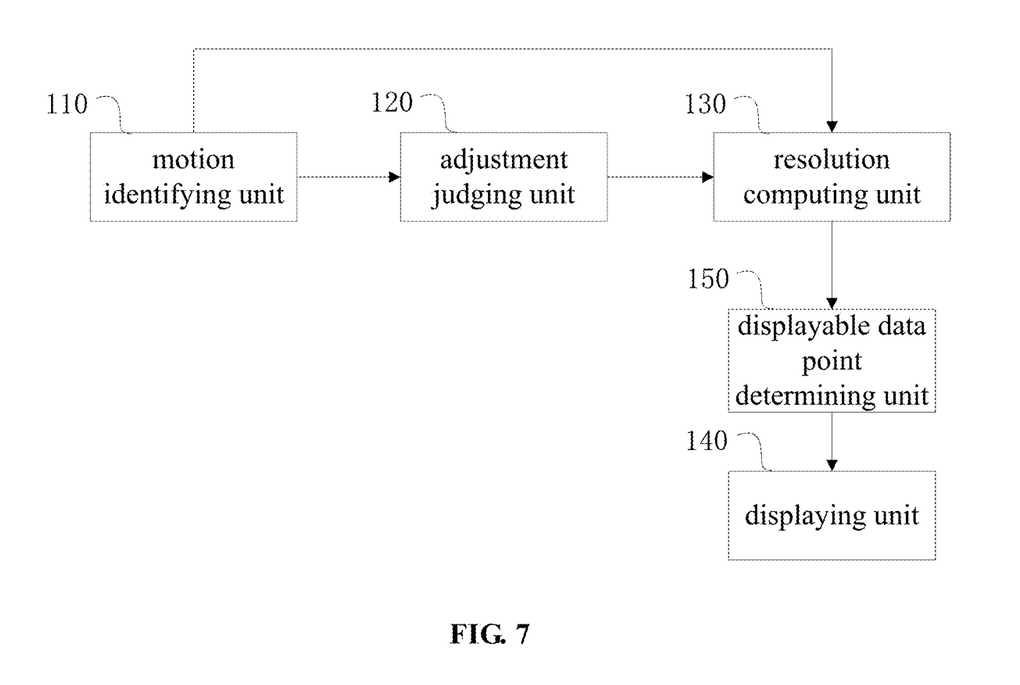
FIG. 7 schematically illustrates a structure of an apparatus for adjusting resolution of a trend chart in another embodiment of the present application.

Based on the above idea, the apparatus for adjusting resolution of trend chart in the embodiment, different from the first embodiment, may further include a displayable data point determining unit. As schematically shown in FIG. 7, the structure of the apparatus for adjusting resolution of trend chart may include a motion identifying unit 110, an adjustment judging unit 120, a resolution computing unit 130, a displayable data point determining unit 150 and a displaying unit 140. The displayable data point determining unit 150 may be used for determining displayable data points corresponding to the adjusted resolution in accordance with the adjusted resolution calculated by the resolution computing unit 130; for example, the displayable data points corresponding to the adjusted resolution may be determined according to different data sampling rates corresponding to different resolutions, or the displayable data points corresponding to the adjusted resolution may be determined according to displayability of the data points under different resolutions. The displaying unit 140 may display the displayable data points with the adjusted resolution in the trend chart.

Figure 8:
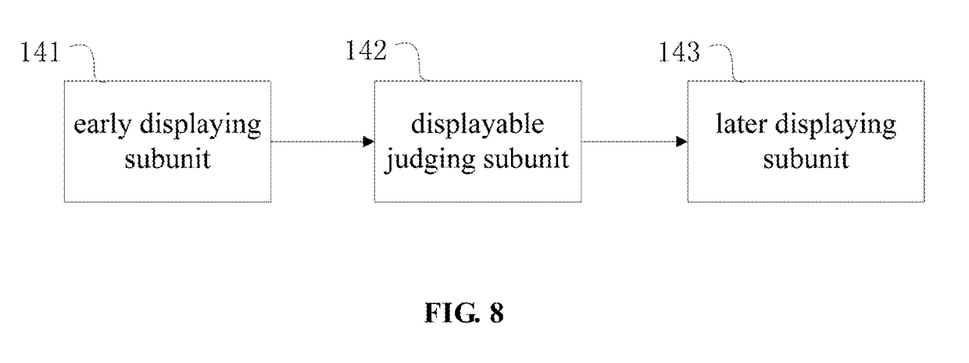
FIG. 8 schematically illustrates a structure of a displaying unit in an embodiment of the present application.

In a specific example, when displaying data with adjusted resolution by the displaying unit 140, processing in a progressive form or an animated form may be used to maintain the continuity of the display. As shown in FIG. 8, the displaying unit 140 may include an early displaying subunit 141, a displayable judging subunit 142 and a later displaying subunit 143. The early displaying subunit 141 may be used for displaying the displayable data points corresponding to original resolution with the adjusted resolution in the trend chart; the displayable judging subunit 142 may be used for identifying the displayability of data points with respect to the original resolution and the adjusted resolution respectively based on the displayable data points corresponding to the adjusted resolution, and accordingly judging whether it is necessary to adjust the data points displayed in the current trend chart; and the later displaying subunit 143 may be used for performing a displaying or concealing process on the data points and adjusting the data points displayed in the trend chart to be the displayable data points corresponding to the adjusted resolution if it is necessary to adjust, and remaining the data points displayed in the trend chart unchanged if it is unnecessary to adjust. For example: if the data points are not displayable with respect to the original resolution but displayable to the adjusted resolution, the later displaying subunit 143 may display the data points in the trend chart in a form of increasing brightness frame by frame; and if the data points are displayable with respect to the original resolution but not displayable with respect to the adjusted resolution, the later displaying subunit 143 may conceal the data points in the trend chart in a form of decreasing brightness frame by frame.

Figure 9:
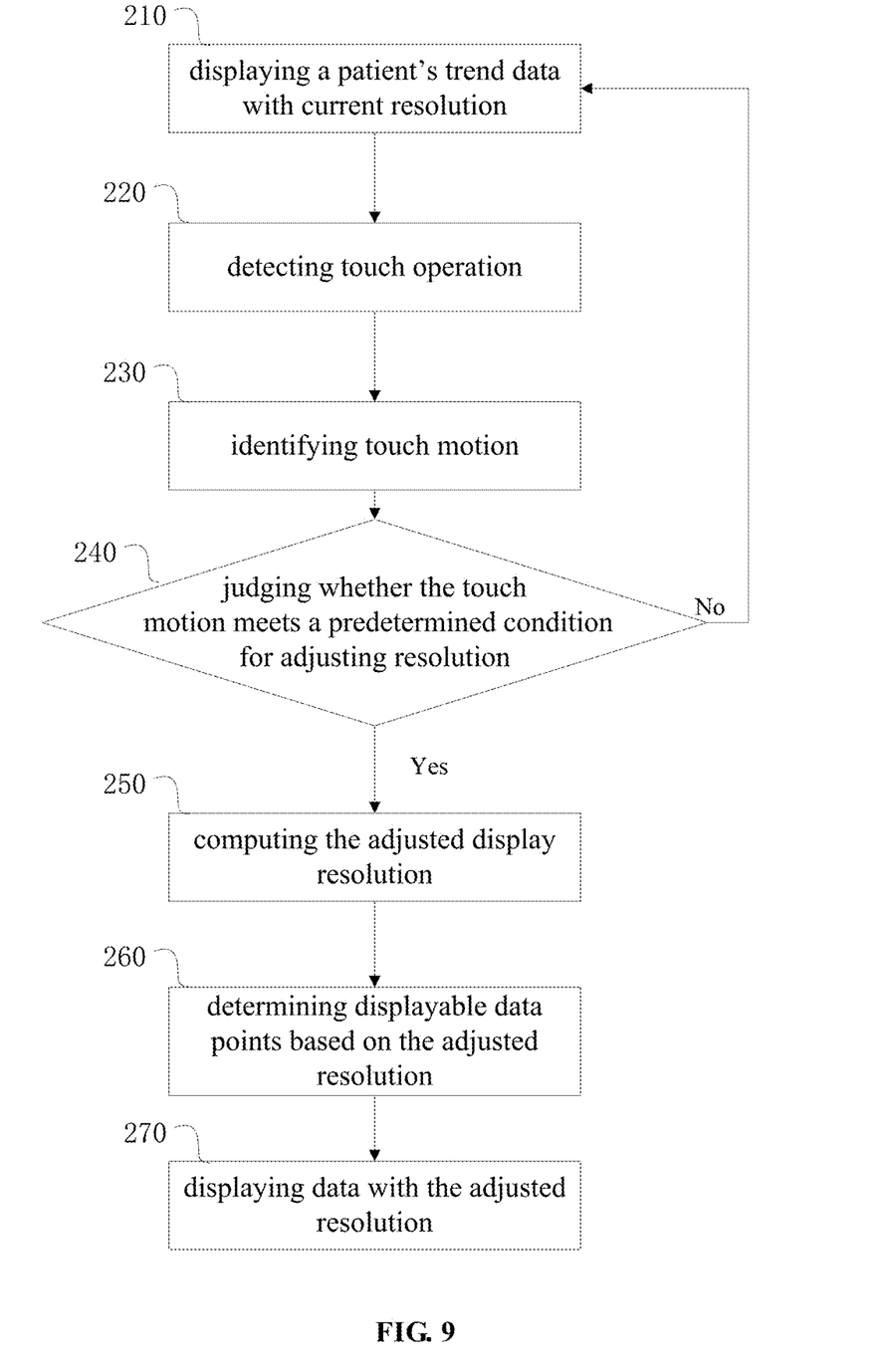
FIG. 9 schematically illustrates a flowchart of adjusting resolution in a trend chart in another embodiment of the present application.

Based on the above idea, the procedure of the method for adjusting resolution, shown in FIG. 9, may add a step 260 between the step 250 and the step 270 compared with the first embodiment. In the step 260, the data points needed to be displayed in the trend chart may be determined based on the adjusted resolution; for example, presetting a corresponding table for resolution and sampling rate, and when determining to adjust resolution, extracting the sampled data based on the data sampling rate corresponding to the adjusted resolution, then the extracted data may be the displayable data points corresponding to the resolution; or checking the displayability of the data points corresponding to the resolution, so as to determine the displayable data point under the resolution.

For example: an instance for displaying in the embodiment is that, the display positions for each point are unconnectedly discrete points, when there are nine displayable data points (P1, P2, P3, P4, P5, P6, P7, P8, P9) in the current display width and the current resolution is Precise1, according to the definition, the data points P1, P3, P5, P7, P9 may be displayable when the resolution is greater than PreciseA, and the data points P2, P4, P6, P8 may be displayable when the resolution is greater than PreciseB, PreciseB>PreciseA, that is, P2, P4, P6, P8 can be displayable with a higher resolution.

When the resolution is adjusted from Precise1 to Precise2, since Precise1>PreciseB, PreciseB>Precise2>PreciseA, then the data points corresponding to Precise2 may be displayed on the interface, i.e., only data points P1, P3, P5, P7, P9 can be displayed. When the resolution is adjusted from Precise2 to Precise1, then the data points corresponding to Precise1 may be displayed on the interface, i.e., all the data points P1, P2, P3, P4, P5, P6, P7, P8, P9 can be displayed.

In this embodiment, different resolution may correspond to different data points, i.e., the data points displayed in the trend chart may be designed based on resolution.

Figure 10:
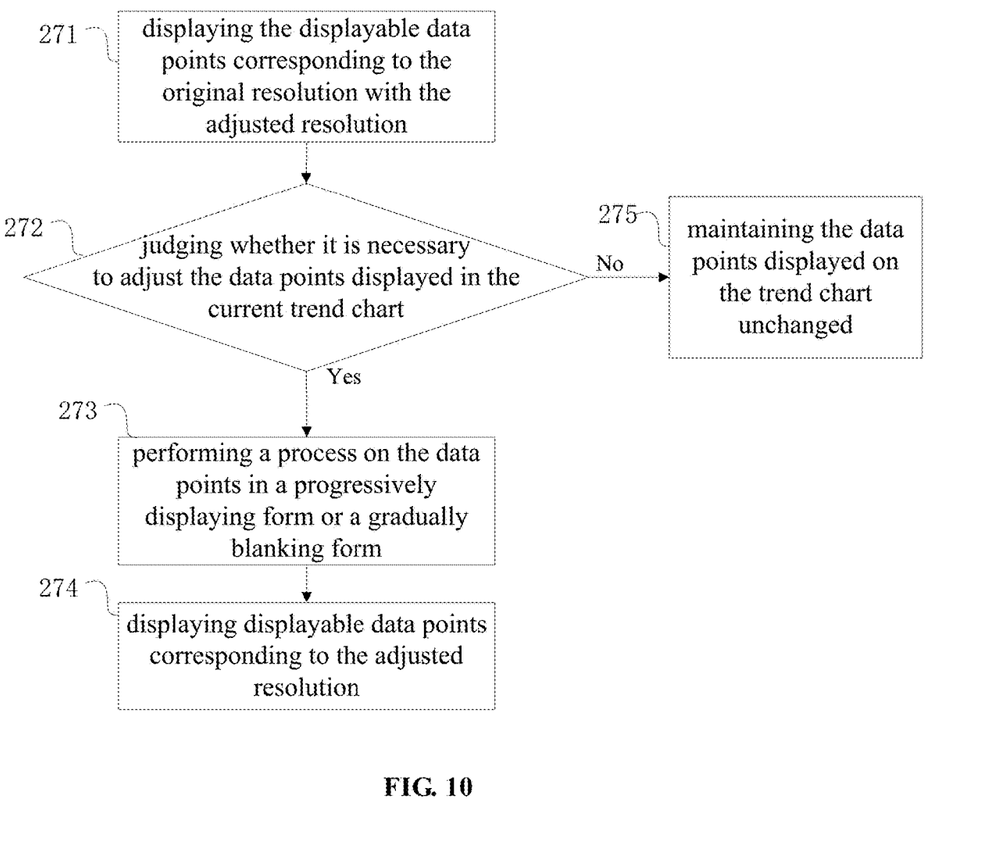
FIG. 10 schematically illustrates a flowchart of displaying a trend chart in an animated form in an embodiment of the present application.

In the step 270, the data points determined by the step 260 may be displayed according to the adjusted resolution. When the data point corresponding to the adjusted resolution is identical to that displayed originally, the display in the step 270 may remain unchanged. When the data point corresponding to the adjusted resolution is different from that displayed originally, the data point displayed in the step 270 may be changed, of which some data points may keep on being displayed, some data points which may not display originally can be displayed according to the data points determined by the new resolution, and other data points which may be displayed originally can be concealed according to the data points determined by the new resolution, i.e., they may not be displayed. When displaying, the data points determined in the step 260 may be displayed directly according to the adjusted resolution; however, there may exist a sudden change in visual effect. To eliminate the sudden change, a process may be performed when the originally displayable data points change to be new data points, making them gradually changed in a progressive form or an animated form. The process, as shown in FIG. 10, may include the following steps:

Step 271, displaying displayable data points corresponding to the original resolution with the adjusted resolution in the trend chart, instead of not directly displaying the data points which can be displayed under the adjusted resolution.

Step 272, judging whether it is necessary to adjust data points that are displayed in the current trend chart based on the displayable data points corresponding to the adjusted resolution; if necessary, performing the step 273, otherwise performing the step 275 to keep the data points displayed on the trend chart unchanged.

Step 273, performing a process on the data points in a progressively displaying form or a gradually concealing form.

If the data points are not displayable with respect to the original resolution but displayable with respect to the adjusted resolution, displaying the data points on the trend chart in a form of increasing brightness frame by frame; and if the data points are displayable with respect to the original resolution but not displayable with respect to the adjusted resolution, concealing the data points on the trend chart in a form of decreasing brightness frame by frame.

Step 274, adjusting the data points displayed on the trend chart to be the displayable data points corresponding to the adjusted resolution.

There may be two manners to display data point on the interface:

1. Displaying in a discrete form. As shown in FIG. 1, the data points may be displayed as discontinuous points.

Figure 11:
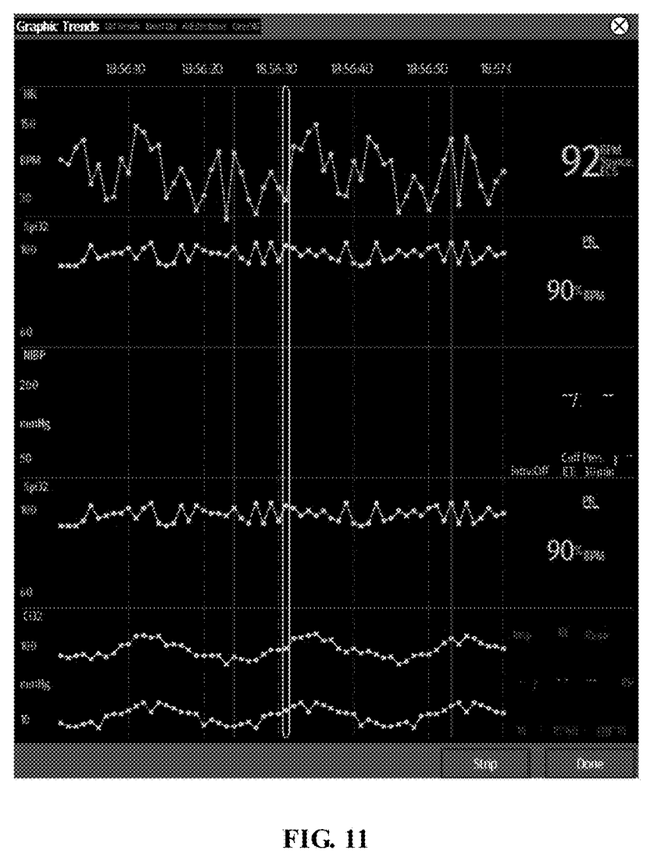
FIG. 11 schematically illustrates another way of displaying a trend chart.

2. Displaying the connecting lines between the points. As shown in FIG. 11, the data points may be displayed as interconnecting points.

In an example of discontinuous points, nine points (P1, P2, P3, P4, P5, P6, P7, P8, P9) are displayed on a current interface, a current resolution is Precise1, the points P1, P3, P5, P7, P9 can be displayable when the resolution is greater than PreciseA, and the points P2, P4, P6, P8 can be displayable when the resolution is greater than PreciseB, PreciseB>PreciseA, that is, P2, P4, P6, P8 can be displayable with a higher resolution.

When the resolution is adjusted from Precise1 to Precise2, since Precise1>PreciseB, PreciseB>Precise2>PreciseA, it may display with Precise2 on the interface and the displayed data points are P1, P2, P3, P4, P5, P6, P7, P8, P9 corresponding to Precise1, then the brightness of the data points P2, P4, P6, P8 may be decreased gradually to be undisplayable within a certain time, and the data points to be displayed finally may be P1, P3, P5, P7, P9 corresponding to Precise2.

When the resolution is adjusted from Precise2 to Precise1, it may display with Precise1 on the interface and the displayed data points are P1, P3, P5, P7, P9 corresponding to Precise2, then the brightness of the data points P2, P4, P6, P8 may be increased gradually to be normal value within a certain time, and the data points to be displayed finally may be P1, P2, P3, P4, P5, P6, P7, P8, P9 corresponding to Precise1.

In an example of interconnecting displayable points, a curved line of nine points (W1, W2, W3, W4, W5, W6, W7, W8, W9) may be displayed on a current interface, a current resolution is Precise1, the points W1, W3, W5, W7, W9 can be displayable when the resolution is greater than PreciseA, and the points W2 W4, W6, W8 can be displayable when the resolution is greater than PreciseB, PreciseB>PreciseA, that is, W2, W4, W6, W8 can be displayable with a higher resolution.

When the resolution is adjusted from Precise1 to Precise2, since Precise1>PreciseB, PreciseB>Precise2>PreciseA, it may display with Precise2 on the interface and the displayed data points are W1, W2, W3, W4, W5, W6, W7, W8, W9 corresponding to Precise1 as well as a curved line Curve1 formed by connection thereof, the data points W2, W4, W6, W8 may be concealed in an animated form later, and the data points W1, W3, W5, W7, W9 corresponding to Precise2 and the curved line Curve2 may be displayed finally. An animated manner changed from Curve1 to Curve2 may be, taking W2 as an example, the brightness of a curved line between W1 and W2, the point W2, and a curved line between W2 and W3 along the Curve1 may be decreased gradually, while a curved line between W1 and W3 along the Curve2 may be increased gradually until the Curve1 is not displayed and the Curve2 is displayed normally; W4, W6, W8 may work in a similar manner.

When the resolution is adjusted from Precise2 to Precise1, it may display with Precise1 on the interface and the displayed data points are W1, W3, W5, W7, W9 corresponding to Precise2 as well as a curved line Curve2 formed by connection thereof, the data points W2, W4, W6, W8 may be displayed in an animated form later, and the data points W1, W2, W3, W4, W5, W6, W7, W8, W9 corresponding to Precise1 and the curved line Curve1 may be displayed finally. An animated manner changed from Curve2 to Curve1 may be, taking W2 as an example, the brightness of a curved line between W1 and W2, the point W2, and a curved line between W2 and W3 along the Curve1 may be increased gradually, while a curved line between W1 and W3 along the Curve2 may be decreased gradually until the Curve1 is displayed normally and the Curve2 is not displayed; W4, W6, W8 may work in a similar manner.

Third Embodiment

Figure 12:
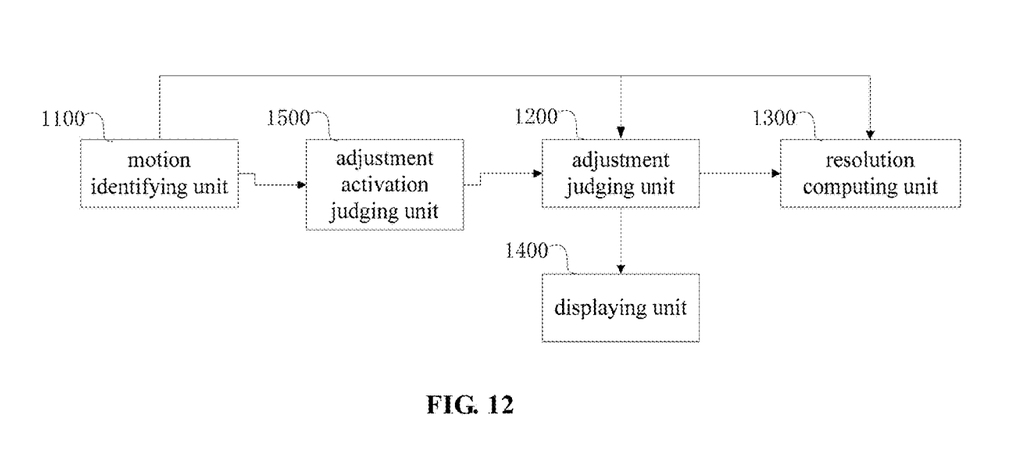
FIG. 12 schematically illustrates a structure of an apparatus for adjusting resolution of a trend chart in another embodiment of the present application.

The procedure may be finished after responding to the touch motion and a next motion detection may be restart in the above embodiment. Unlike the above embodiment, in this embodiment, the touch motion may include a motion for activating resolution adjustment and a motion for adjusting resolution. Please referring to FIG. 12, the apparatus for adjusting resolution of trend chart may include a motion identifying unit 1100, an adjustment activation judging unit 1500, an adjustment judging unit 1200, a resolution computing unit 1300 and a displaying unit 1400. The motion identifying unit 1100 may be used for receiving touch information outputted by the touch screen, identifying motion of user's touch operation in accordance with the touch information and generating motion information; the adjustment activation judging unit 1500 may be used for judging whether the touch motion corresponds to a predetermined activation for adjusting resolution, if no, maintaining the digital image displayed on the interface with original resolution, if the touch motion corresponds to the predetermined activation for adjusting resolution, starting a process of adjusting resolution on the interface; the adjustment judging unit 1200 may be used for, after starting the process of adjusting resolution by the adjustment activation judging unit, judging whether the touch motion detected by the motion identifying unit meets a predetermined condition for adjusting resolution; the resolution computing unit 1300 may be used for, if the adjustment judging unit determines that the touch motion meets the predetermined condition for adjusting resolution, computing adjusted resolution based on the motion information and a predetermined computing method; and the displaying unit 1400 may be used for displaying the digital image with the adjusted resolution outputted by the resolution computing unit on a region desired to be adjusted on the interface, and maintaining the digital image displayed on the interface with original resolution if the detected touch motion fails to meet the predetermined condition for adjusting resolution.

Figure 13:
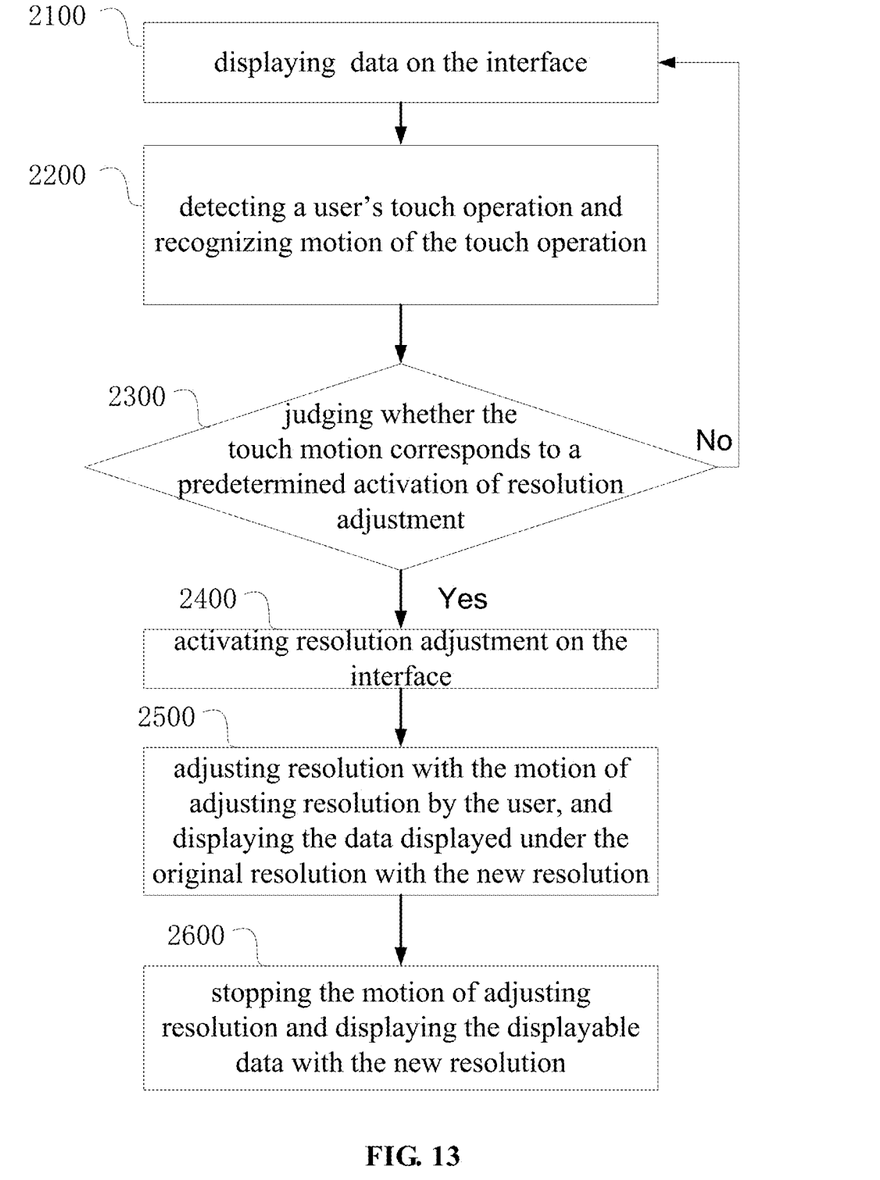
FIG. 13 schematically illustrates a flowchart of adjusting resolution in a trend chart in still another embodiment of the present application.

Based on this embodiment, the procedure of the method for adjusting resolution, shown in FIG. 13, may include the following steps:

Step 2100, keeping an interface of the trend chart open on the monitor and displaying a patient's trend data with a current resolution, where the initial state is displaying data on the interface.

Step 2200, detecting user's touch operation and recognizing motion of the touch operation. When a user desires to adjust the resolution on the interface, the user may contact with the touch screen and perform touch operation to change the display resolution to be that desired by the user. The step is an interaction between the user and the monitor.

An example of a predetermined activation for starting resolution adjustment may be represented by operation of two fingers and two touch points, when the two fingers touch the touch screen and the distance between the two fingers is generated, it is regarded as an activation motion.

Step 2300, identifying the user's motion, and judging whether the detected touch motion corresponds to a predetermined activation of resolution adjustment, if yes, turning to perform step 2400 to start resolution adjustment; and if no, keeping to display the patient's trend data with current resolution without responding to the user's motion.

Step 2500, adjusting resolution with the motion of adjusting resolution by the user, and displaying the data which displayed under the original resolution with the new resolution. The step, in which new display resolution may be calculated according to the information of adjusting motion and the adjusting method for the resolution, can be performed by the scheme described in the above embodiment, or can adopt the following scheme:

The predetermined motion for activating resolution adjustment and the motion of adjusting resolution may be sliding two fingers on the touch screen. When detecting an increment of the distance between two touch points, according to the judgment of the step 2300, the resolution adjustment may be activated. Then the distance of the two touch points is detected, and the adjusted resolution may be calculated according to the distance between the two touch points. The points detected initially by the motion for activating resolution adjustment may be updated to the current touching position in each calculation for the motion of adjusting resolution. The resolution may be decreased when the distance between the two fingers reduces, and the displaying time period on a single screen may become larger; while the resolution may be increased when the distance between the two fingers enlarges, and the displaying time period on a single screen may become smaller. The motion may be considered to be finished when the user's two fingers leave the touch screen.

Step 2600, stopping the motion of adjusting resolution and displaying the displayable data with the new resolution on the interface to finish all the resolution adjustment.

Those skilled in the art can appreciate that all or part of the steps of the various methods in the above-described embodiments may be accomplished by instructing relevant hardware through program which may be stored in a computer readable storage medium which may include: a read-only memory, random access memory, magnetic or optical disk.

Though the present application has been described in detailed with aforesaid embodiments, the present application is not limited by these embodiments. It can be understood by those skilled in the art that various simple deduction or replacement can be made without departing from the spirit of the present application.

The invention claimed is:

1. A method for adjusting a time range represented by a displayed width of a trend chart using a touch screen of a patient monitor as a display and input device, comprising:
   detecting a touch operation inputted by a user through the touch screen while displaying the trend chart on an interface and generating touch information, wherein the touch operation includes at least three touch points that define a geometric shape enclosed by the at least three touch points;
   identifying touch motion of the user for the touch operation in accordance with the touch information and generating motion information;
   judging whether the touch motion meets a predetermined condition for adjusting the time range according to the motion information, wherein the predetermined condition comprises detecting a touch motion at a region of the trend chart including a plurality of sliding touch points;
   if yes, computing an adjusted time range based on the motion information and a predetermined computing method and displaying the trend chart such that the displayed width of the trend chart represents the adjusted time range on a region desired to be adjusted on the interface; wherein the touch motion corresponds to a predetermined motion for adjusting the time range includes sliding the at least three touch points, and wherein computing the adjusted time range based on the motion information and the predetermined computing method comprises:
   calculating initial geometrical quantity for a plurality of touch points based on location information of the plurality of touch points in the motion information when they initially contact the touch screen;
   calculating after-sliding geometrical quantity for the plurality of touch points based on final location information of the plurality of touch points in the motion information; and
   calculating the adjusted time range based on the following formula:

$$G1/G2 = Precise1/Precise2$$

where $G1$ is the initial geometrical quantity, $G2$ is the after-sliding geometrical quantity, $Precise1$ is an original time range and $Precise2$ is the adjusted time range; and wherein the geometrical quantity is an area of the geometrical shape enclosed by the at least three touch points; and if no, maintaining the trend chart displayed on the interface with the original time range; and wherein a number of data points in the trend chart corresponding to the adjusted time range is more than a number of data points in the same time range as the adjusted time range in the trend chart corresponding to the original time range, when the adjusted time range is smaller than the original time range.

2. A method according to claim 1, further comprising:

judging whether the touch motion corresponds to a predetermined activation for adjusting the time range according to the motion information: if no, maintaining an original time range on the interface; if yes, applying the method according to claim 1 to adjust the time range represented by the displayed width of the trend chart using the touch screen of the patient monitor as the display and input device.

3. The method according to claim 1, wherein the trend chart comprises a trend chart of physiological parameters varied with time.

4. The method according to claim 3, wherein judging whether the touch motion meets a predetermined condition for adjusting the time range according to the motion information comprises:

judging whether the touch motion corresponds to a predetermined motion for adjusting the time range.

5. The method according to claim 3, wherein displaying the trend chart with the adjusted time range on a region desired to be adjusted on the interface comprises:

determining displayable data points corresponding to the adjusted time range; and displaying the displayable data points with the adjusted time range in the trend chart.

6. The method according to claim 5, wherein displaying the displayable data points with the adjusted time range in the trend chart comprises:

displaying displayable data points corresponding to the original time range with the adjusted time range in the trend chart;

judging whether it is necessary to adjust data points that are displayed in the current trend chart based on the displayable data points corresponding to the adjusted time range;

if necessary, displaying or concealing the data points and adjusting the data points displayed on the trend chart to be the displayable data points corresponding to the adjusted time range; and if unnecessary, keeping the data points displayed on the trend chart unchanged, wherein displaying or concealing comprises:

if the data points are not displayable with respect to the original time range but displayable with respect to the adjusted time range, displaying the data points on the trend chart in a form of increasing brightness frame by frame; and if the data points are displayable with respect to the original time range but not displayable with respect to the adjusted time range, concealing the data points on the trend chart in a form of decreasing brightness frame by frame.

7. The method according to claim 5, wherein the displayable data points corresponding to the adjusted time range are determined according to different data sampling rates corresponding to different time range; or the displayable data points corresponding to the adjusted time range are determined according to displayable character of the data points under different time range.

8. The method according to claim 3, wherein the motion information comprises at least location information of the touch operation, and judging whether the touch motion meets a predetermined condition for adjusting the time range according to the motion information further comprises:

judging whether the touch motion is located at a display region of the trend chart based on the location information of the touch operation: if no, the touch motion is regarded as failing to meet the predetermined condition for adjusting the time range; if yes, and the touch motion corresponds to a predetermined motion for adjusting the time range, the touch motion is regarded as meeting the predetermined condition for adjusting the time range.

9. An apparatus for adjusting a time range represented by a displayed width of a trend chart using a touch screen of a patient monitor as a display and input device, comprising:

a motion identifying unit for receiving touch information outputted by the touch screen, identifying touch motion of a user's touch operation in accordance with the touch information and generating motion information, wherein the touch operation includes at least three touch points that define a geometric shape enclosed by the at least three touch points;

an adjustment judging unit for judging whether the touch motion detected by the motion identifying unit meets a predetermined condition for adjusting the time range according to the motion information, wherein the predetermined condition comprises detecting a touch motion at a region of the trend chart including a plurality of sliding touch points;

a time range computing unit for computing an adjusted time range based on the motion information and a predetermined computing method if the adjustment judging unit determines that the touch motion meets the predetermined condition for adjusting the time range;

wherein the touch motion corresponds to a predetermined motion for adjusting the time range includes sliding the at least three touch points, and wherein computing the adjusted time range based on the motion information and the predetermined computing method comprises:

calculating initial geometrical quantity for a plurality of touch points based on location information of the plurality of touch points in the motion information when they initially contact the touch screen;

calculating after-sliding geometrical quantity for the plurality of touch points based on final location information of the plurality of touch points in the motion information; and calculating the adjusted time range based on the following formula:

$$G1/G2 = Precise1/Precise2$$

where G1 is the initial geometrical quantity, G2 is the after-sliding geometrical quantity, Precise1 is an original time range and Precise2 is the adjusted time range; and wherein the geometrical quantity is an area of the geometrical shape enclosed by the at least three touch points; and a displaying unit for displaying the trend chart with a displayed width corresponding to the adjusted time range outputted by the computing unit on a region desired to be adjusted on the interface, and maintaining the trend chart displayed on the interface with the original time range if the detected touch motion fails to meet the predetermined condition of adjusting the time range; and wherein a number of data points in the trend chart corresponding to the adjusted time range is more than a number of data points in the same time range as the adjusted time range in the trend chart corresponding to the original time range, when the adjusted time range is smaller than the original time range.

10. The apparatus according to claim 9, further comprising:

an adjustment activation judging unit for judging whether the touch motion corresponds to a predetermined activation for adjusting the time range, if no, maintaining the trend chart displayed on the interface with the original time range; if the touch motion corresponds to the predetermined activation for adjusting the time range, applying the method according to claim 1 to adjust the time range represented by the displayed width of the trend chart using the touch screen of the patient monitor as the display and input device.

11. The apparatus according to claim 10 wherein the adjustment judging unit is configured for judging whether the touch motion corresponds to a predetermined motion for adjusting the time range.

12. The apparatus according to claim 10, wherein the motion information comprises at least location information of the touch operation, and the adjustment judging unit is configured for judging whether the touch motion is located at a display region of the trend chart based on the location information of the touch operation, if no, the touch motion is regarded as failing to meet a predetermined condition for adjusting the time range; if yes, and the touch motion corresponds to a predetermined motion for adjusting the time range, the touch motion is regarded as meeting the predetermined condition for adjusting the time range.

13. The apparatus according to claim 12,
wherein the displaying unit comprises:
an early displaying subunit for displaying the displayable data points corresponding to original time range with the adjusted time range in the trend chart;
a displayable judging subunit for judging whether it is necessary to adjust the data points displayed in the current trend chart according to the displayable data points corresponding to the adjusted time range; and
a later displaying subunit for performing a displaying or concealing process on the data points and adjusting the data points displayed in the trend chart to be the displayable data points corresponding to the adjusted time range if necessary to adjust, and remaining the data points displayed in the trend chart unchanged if it is unnecessary to adjust;
wherein the displayable judging subunit is configured for identifying the displayable data points with respect to the original time range and the adjusted time range respectively, and the later displaying subunit is configured for displaying the data points in the trend chart in a form of increasing brightness frame by frame if the data points are not displayable with respect to the original time range but displayable to the adjusted time range, and concealing the data points in the trend chart in a form of decreasing brightness frame by frame if the data points are displayable with respect to the original time range but not displayable with respect to the adjusted time range.

14. The apparatus according to claim 13, wherein the displayable data points corresponding to the adjusted time range are determined according to different data sampling rates corresponding to different time range; or the displayable data points corresponding to the adjusted time range are determined according to displayable character of the data points under different time range.

15. The apparatus according to claim 9, wherein the trend chart comprises a trend chart of physiological parameters varied with time.

16. A medical device, comprising:
a data detecting device for detecting a patient's life sign parameters; and
a data processing module with an input terminal coupled to an output terminal of the data detecting device for analyzing and processing the life sign parameters to generate visual display data;
a touch screen, which is a multi-touch screen connected to the data processing module by signals, configured for providing a visual trend chart of the life sign parameters and a user input interface for a monitor and outputting touch information when sensing a user's operation; and
an apparatus for adjusting a time range represented by a displayed width of a trend chart using the touch screen, comprising:
a motion identifying unit for receiving touch information outputted by the touch screen, identifying touch motion of a user's touch operation in accordance with the touch information and generating motion information, wherein the touch operation includes at least three touch points that define a geometric shape;
an adjustment judging unit for judging whether the touch motion detected by the motion identifying unit meets a predetermined condition for adjusting the time range according to the motion information, wherein the predetermined condition comprises detecting a touch motion at a region of the trend chart including a plurality of sliding touch points;
a time range computing unit for computing an adjusted time range based on the motion information and a predetermined computing method if the adjustment judging unit determines that the touch motion meets the predetermined condition for adjusting the time range; wherein the touch motion corresponds to a predetermined motion for adjusting the time range includes sliding the at least three touch points, and wherein computing the adjusted time range based on the motion information and the predetermined computing method comprises:
calculating initial geometrical quantity for a plurality of touch points based on location information of the plurality of touch points in the motion information when they initially contact the touch screen;
calculating after-sliding geometrical quantity for the plurality of touch points based on final location information of the plurality of touch points in the motion information; and
calculating the adjusted time range based on the following formula:

$$G1/G2 = Precise1/Precise2$$

where G1 is the initial geometrical quantity, G2 is the after-sliding geometrical quantity, Precise1 is an original time range and Precise2 is the adjusted time range; and wherein the geometrical quantity is an area of the geometrical shape enclosed by the at least three touch points; and a displaying unit for displaying the trend chart with a displayed width corresponding to the adjusted time range outputted by the computing unit on a region desired to be adjusted on the interface, and maintaining the trend chart displayed on the interface with the original time range if the detected touch motion fails to meet the predetermined condition of adjusting the time range; and wherein a number of data points in the trend chart corresponding to the adjusted time range is more than a number of data points in the same time range as the adjusted time range in the trend chart corresponding to the original time range, when the adjusted time range is smaller than the original time range; wherein the apparatus for adjusting the time range is connected to the touch screen and the data processing module by signals respectively, and receives the touch information outputted by the touch screen, and outputs a displaying result with the adjusted time range to the data processing module.

17. The medical device according to claim 16, wherein the medical device is a patient monitor, a central station, a defibrillator, or an anesthesia machine.

* * * * *